United States Patent
Wang et al.

(10) Patent No.: US 10,092,257 B2
(45) Date of Patent: Oct. 9, 2018

(54) DYNAMIC BOWTIE FILTER FOR CONE-BEAM/MULTI-SLICE CT

(71) Applicants: Ge Wang, Loudonville, NY (US); Fenglin Liu, Troy, NY (US); Wenxiang Cong, Albany, NY (US); Qingsong Yang, Troy, NY (US)

(72) Inventors: Ge Wang, Loudonville, NY (US); Fenglin Liu, Troy, NY (US); Wenxiang Cong, Albany, NY (US); Qingsong Yang, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 290 days.

(21) Appl. No.: 14/924,495

(22) Filed: Oct. 27, 2015

(65) Prior Publication Data

US 2016/0113602 A1    Apr. 28, 2016

Related U.S. Application Data

(60) Provisional application No. 62/068,843, filed on Oct. 27, 2014.

(51) Int. Cl.
*A61B 6/00* (2006.01)
*A61B 6/03* (2006.01)

(52) U.S. Cl.
CPC ............ *A61B 6/4035* (2013.01); *A61B 6/032* (2013.01); *A61B 6/544* (2013.01); *A61B 6/583* (2013.01); *A61B 6/482* (2013.01)

(58) Field of Classification Search
CPC ............... H04N 1/4051; H04N 1/4055; H04N 1/32229; H04N 1/32251; H04N 1/32256; H04N 1/32304; H04N 1/32309; H04N 1/40; H04N 1/4053; H04N 1/52; H04N 2201/3205; H04N 2201/3271; A61B 6/032; A61B 6/4035; A61B 6/482; A61B 6/544; A61B 6/583; A61B 6/542; A61B 6/4488; A61B 6/488; A61B 6/027; A61B 6/035; A61B 6/4241; A61B 6/06; A61B 6/4085;

(Continued)

(56) References Cited

U.S. PATENT DOCUMENTS 4,497,062 A * 1/1985 Mistretta .................. G21K 1/10
                                                                 378/158
6,724,499 B1   4/2004 Satoh
(Continued)

OTHER PUBLICATIONS

Ballabriga, R. et al., "Medipix3: A 64 k pixel detector readout chip working in single photon counting mode with improved spectrometric performance," *Nuclear Instruments & Methods in Physics Research Section a-Accelerators Spectrometers Detectors and Associated Equipment*, 633, S15-S18 (2011).

(Continued)

*Primary Examiner* — Irakli Kiknadze
(74) *Attorney, Agent, or Firm* — Murtha Cullina LLP; Anthony P. Gangemi

(57) ABSTRACT

Dynamic bowties, imaging systems including a bowtie, and methods of imaging including such bowties or systems are provided. A bowtie can be a three-dimensional (3-D) dynamic bowtie and can include a highly-attenuating bowtie (HB) and a weakly-attenuating bowtie (WB). The HB can be filled with a liquid, and the WB can be immersed in the liquid of the HB.

17 Claims, 11 Drawing Sheets

(58) Field of Classification Search
CPC ... A61B 6/5205; A61B 6/4028; A61B 6/4042; A61B 6/4441; A61B 6/405
USPC .................................. 378/4, 19, 16, 156–159
See application file for complete search history.

(56) References Cited

U.S. PATENT DOCUMENTS

| | | | | |
|---|---|---|---|---|
| 7,308,073 | B2* | 12/2007 | Tkaczyk | G21K 1/10 378/156 |
| 7,433,443 | B1* | 10/2008 | Tkaczyk | A61B 6/032 378/19 |
| 9,329,140 | B2* | 5/2016 | Zou | G01N 23/046 |
| 9,390,825 | B2* | 7/2016 | Lee | G21K 1/10 |
| 9,818,182 | B2* | 11/2017 | Ueki | G06T 7/0012 |
| 2005/0013411 | A1* | 1/2005 | Yahata | A61B 6/06 378/156 |
| 2005/0089136 | A1* | 4/2005 | Toth | A61B 6/032 378/16 |
| 2014/0294139 | A1* | 10/2014 | Funk | A61B 6/06 378/16 |

OTHER PUBLICATIONS

Bartolac, S. et al., "Fluence field optimization for noise and dose objectives in CT," *Medical Physics*, 38, S2-S17 (2011).

Berrington de Gonzalez,A. et al. "Risk of cancer from diagnostic X-rays: estimates for the UK and 14 other countries," *Lancet*, 363, 345-351 (2004).

Blessing, M. et al. "Kilovoltage beam model for flat panel imaging system with bow-tie filter for scatter prediction and correction," *Physica Medica—European Journal of Medical Physics*, 28, 134-143 (2012).

Bogue, R. et al., "3D printing: the dawn of a new era in manufacturing?," *Assembly Automation*, 33, 307-311 (2013).

Boone, J.M. , "Method for evaluating bow tie filter angle-dependent attenuation in CT: Theory and simulation results," *Medical Physics*, 37, 40-48 (2010).

Gaisberger, C. et al., "Three-dimensional surface scanning for accurate patient positioning and monitoring during breast cancer radiotherapy," *Strahlentherapie Und Onkologie*, 189, 887-893 (2013).

Gies, M. et al. "Dose reduction in CT by anatomically adapted tube current modulation. I. Simulation studies," *Medical physics*, 26, 2235 (1999).

Hsieh, S.S. et. al. "The feasibility of a piecewise-linear dynamic bowtie filter," *Medical Physics*, 40, (2013).

Image Gently ® Campaign, [online, webpage retrieved Nov. 20, 2015] , www.imagegently.org.

Kalender, W.A. et al. "Dose reduction in CT by anatomically adapted tube current modulation. II. Phantom measurements," *Medical physics*, 26, 2248 (1999).

Liu, F, et al. "Dynamic Bowtie Filter for Cone-Beam/Multi-Slice CT," published Jul. 22, 2014, http://journals.plos.org/plosone/article?id=10.1371/journal.pone.0103054.

Liu, F. et al. "Dynamic bowtie for fan-beam CT," Journal of X Ray Science and Technology, 21, 579-590 (2013).

Mail, N. et al., "The influence of bowtie filtration on cone-beam CT image quality," *Medical Physics*, 36, 22-32 (2009).

Mavroidis, C. et al. "Patient specific ankle-foot orthoses using rapid prototyping," *Journal of Neuroengineering and Rehabilitation*, 8 (2011).

McKenney, S.E. et al., "Experimental validation of a method characterizing bow tie filters in CT scanners using a real-time dose probe," *Medical Physics*, 38, 1406-1415 (2011).

Mutic, S. et al. "Quality assurance for computed-tomography simulators and the computedtomography-simulation process: Report of the AAPM radiation therapy committee task group No. 66," *Medical Physics*, 30, 2762-2792 (2003).

National Technical Information Serivice, Visible Human Project, [online, webpage retrieved Nov. 20, 2015], http://www.ntis.gov/products/vishuman.aspx.

Peppler, W. et al. "A Digitally Controlled Beam Attenuator," *American Journal of Roentgenology*, 139, 426-426 (1982). (Abstract only).

Taguchi, K. et al., "An analytical model of the effects of pulse pileup on the energy spectrum recorded by energy resolved photon counting x-ray detectors," *Medical Physics*, 37, 3957-3969 (2010).

Toshiba, Low Dose Solution of CT Hardware, [online web page retrieved Nov. 20, 2015], www.toshibamedicalsystems.com/tmd/english/products/dose/lowdose/hardware.html.

Toth, T. et al., "Image quality and dose optimization using novel x-ray source filters tailored to patient size," *Medical Imaging 2005: Physics of Medical Imaging*, Pts 1 and 2, 5745, 283-291 (2005). (Abstract only).

Wang, W. et al. "Cost-effective Printing of 3D Objects with Skin-Frame Structures," *Acm Transactions on Graphics*, 32 (2013).

Whiting, B. et al. "The Influence of Bowtie Filters on X-Ray CT Signals," Medical Physics, 32 (2005). (Abstract only).

X-Ray Mass Attenuation Coefficients-A.150 Tissue-Equivalent Plastic, [online, webpage retrieved Nov. 5, 2015] http://physics.nist.gov/PhysRefData/XrayMassCoef/ComTab/c552.html.

X-Ray Mass Attenuation Coefficients-Aluminum, [online, webpage retrieved Nov. 5, 2015] http://physics.nist.gov/PhysRefData/XrayMassCoef/ElemTab/z13.html.

Zeng, G.S.L. et al. "Nonuniform noise propagation by using the ramp filter in fan-beam computed tomography," *Ieee Transactions on Medical Imaging*, 23, 690-695 (2004).

* cited by examiner

DYNAMIC BOWTIE FILTER FOR CONE-BEAM/MULTI-SLICE CT

CROSS-REFERENCE TO A RELATED APPLICATION

The present application claims the benefit of U.S. Provisional Application Ser. No. 62/068,843, filed Oct. 27, 2014, which is incorporated by reference herein in its entirety, including any figures, tables, and drawings.

BACKGROUND OF INVENTION

X-ray computed tomography (CT) is an important imaging tool in modern hospitals and clinics, and it is still under rapid development. Two areas that are of particular concern are radiation dose reduction and multi-energy imaging, and these two areas are interconnected. CT radiation dose is a public major concern, especially for children. A British study quantified the cancer risk associated with the use of diagnostic x-rays, arguably causing about 700 cases of cancer per year in Britain and >5,600 cases in US. Hence, the well-known ALARA ("As Low As Reasonably Achievable") principle has been accepted. Also, a more recent Image Gently® campaign (www.imagegently.org) has generated a positive impact for all patients. Hence, it is ideal to send X-ray photons along each path as seldom as possible.

CT contrast resolution is rather poor in the context of soft tissue imaging. X-ray detection technology has been almost exclusively based on energy-integration. On the other hand, the best photon-counting detectors recognize photons individually and spectrally. Photon-counting detectors can reveal elemental composition and support contrast-enhanced studies through K-edge imaging. Medipix is a series of state-of-the-art photon-counting detectors for X-ray imaging. However, the dynamic range of the photon-counting detector is rather limited. When the flux on the detector is lower than the maximum count rate, the imaging performance can be good, but if multiple photons arrive in temporal proximity, the detector may not be able to resolve them as separate events. This loss results in spectral distortion.

BRIEF SUMMARY

The subject invention provides novel and advantageous imaging bowties (or bowtie filters), imaging systems including a bowtie, and methods of imaging including such bowties or systems. A bowtie can be a three-dimensional (3-D) dynamic bowtie and can include a highly-attenuating bowtie (HB) and a weakly-attenuating bowtie (WB). The HB can be filled with a liquid (e.g., a heavy liquid), and the WB can be immersed in the liquid of the HB. The HB can be configured to target a balanced flux distribution on a detector or detector array when no object is in the imaging field of view (FOV). The WB can be configured to compensate for an object in the imaging FOV and therefore can be, for example, a scaled-down version of the object in the FOV (e.g., the object to be imaged). The WB can be configured to be rotated and/or translated in synchrony with the source rotation and/or object (the object to be imaged, such as a patient) translation; this can result in the overall flux balance being maintained on the detector or the detector array. Embodiments of the subject invention can advantageously be used for cone-beam and/or multi-slice computed tomography (CT) imaging or scanning (e.g., X-ray CT). Embodiments of the subject invention can also be used for fan-beam CT imaging or scanning (fan-beam geometry is a special case of cone-beam geometry).

Related art bowtie filters produce attenuation profiles that are fixed and cannot be adaptively changed with gantry rotation during imaging. Although modern CT scanners can employ a small number of bowtie filters for different applications, these filters are not personalized and must be fixed for an entire scan. Dynamic bowties of the subject invention can include a rotating WB (e.g., a solid WB) in a stationary HB (e.g., a liquid HB). The HB can include a liquid, such as a highly-attenuating liquid, thereby allowing dynamic compensation to be realized in cone-beam geometry, making possible circular and spiral multi-slice/cone-beam scanning modes.

In an embodiment, a dynamic bowtie filter can include: a HB including a liquid contained within a first container; and a WB immersed within the liquid of the HB and including a second container.

In another embodiment, a CT imaging device can include: a radiation source; a detector to receive radiation after it passes through an object to be imaged; and a dynamic bowtie filter. The dynamic bowtie filter can include: a HB including a liquid contained within a first container; and a WB immersed within the liquid of the HB and including a second container.

In yet another embodiment, a method of imaging an object using CT can include: positioning the object within the FOV of a CT imaging device; and providing radiation from a radiation source of the CT imaging device such that a detector of the CT imaging device receives at least a portion of the radiation after it passes through the object. The CT imaging device can be as described above. The WB can rotate in synchrony with the radiation source and translate in synchrony with the object while the radiation source provides radiation.

DETAILED DISCLOSURE

Figure 1A:
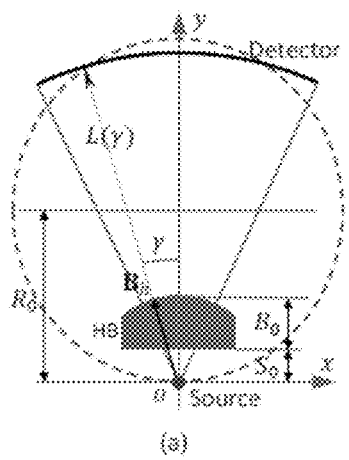
FIG. 1A shows a dynamic bowtie in fan-beam geometry.

The subject invention provides novel and advantageous imaging bowties (or bowtie filters), imaging systems including a bowtie, and methods of imaging including such bowties or systems. A bowtie can be a three-dimensional (3-D) dynamic bowtie and can include a highly-attenuating bowtie (HB) and a weakly-attenuating bowtie (WB). The HB can be filled with a liquid (e.g., a heavy liquid such as a liquid with a density greater than that of water), and the WB can be immersed in the liquid of the HB. The HB can be configured to target a balanced flux distribution on a detector or detector array when no object is in the imaging field of view (FOV). The WB can be configured to compensate for an object in the imaging FOV and therefore can be, for example, a scaled-down version of the object in the FOV (e.g., the object to be imaged). The WB can be configured to be rotated and/or translated in synchrony with the source rotation and/or object (the object to be imaged, such as a patient) translation; this can result in the overall flux balance being maintained on the detector or the detector array. Embodiments of the subject invention can advantageously be used for cone-beam and/or multi-slice computed tomography (CT) imaging or scanning (e.g., X-ray CT). Embodiments of the subject invention can also be used for fan-beam CT imaging or scanning (fan-beam geometry is a special case of cone-beam geometry).

Due at least in part to the spectral distortion present in related art imaging techniques, it is highly desirable to prescribe attenuated photon flux on a per-ray basis. In addition, optimally balancing an attenuated X-ray flux distribution is important for CT dose reduction and multi-energy CT. A pre-patient attenuator, such as a bowtie filter (or "bowtie") can be used. A bowtie filter can selectively attenuate photons emitted from an X-ray source as a function of the angle of an X-ray. Thus, the bowtie can compress the dynamic range on the detector by increasing attenuation for X-rays further from the iso-center of a FOV, which typically travel through less tissue. Thus, the bowtie helps improve image quality; because readings of the detectors can be substantially equalized, the dynamic range can be reduced for more detailed information quantization. Also, by blocking low-energy X-rays, the bowtie can also works with an X-ray beam filter to reduce the beam-hardening effect. Further, by blocking radiation to the periphery of a patient where the attenuation path is the shortest, the radiation dose and the scatter-to-primary ratio can be reduced.

Related art bowtie filters produce an attenuation profile that is fixed and cannot be adaptively changed with gantry rotation. Although modern CT scanners employ a small number of bowtie filters for different applications, these filters are not personalized and must be fixed for an entire scan. An attenuation-based tube current modulation method can be used to attempt to reduce radiation dose. Such a method modulates an incoming X-ray flux as a function of the view angle, instead of the angle of an individual X-ray. Hence, the tube current modulation can be customized on a per-patient basis. However, this modulation changes neither the scatter-to-primary ratio nor the dynamic range for any given view angle.

The combination of a related art bowtie filter and a tube current modulation cannot meet the sophisticated needs for CT dose reduction and multi-energy imaging. Dynamic bowtie filters of the subject invention, though, can address these needs. Each of the following references discloses aspects of bowtie filters and is incorporated herein by reference in its entirety: G. S. L. Zeng, "Nonuniform noise propagation by using the ramp filter in fan-beam computed tomography," Ieee Transactions on Medical Imaging 23, 690-695 (2004); T. Toth, E. Cesmeli, A. Ikhlef, T. Horiuchi, M. Flynn, "Image quality and dose optimization using novel x-ray source filters tailored to patient size," Medical Imaging 2005: Physics of Medical Imaging, Pts 1 and 2 5745, 283-291 (2005); N. Mail, D. J. Moseley, J. H. Siewerdsen, D. A. Jaffray, "The influence of bowtie filtration on cone-beam CT image quality," Medical Physics 36, 22-32 (2009); S. S. Hsieh, N. J. Pelc, "The feasibility of a piecewise-linear dynamic bowtie filter," Medical Physics 402013); F. Liu, G. Wang, W. Cong, S. Hsieh, N. Pelc, "Dynamic bowtie for fan-beam CT," Journal of X-Ray Science and Technology 21, 579-590 (2013); E. Roessl, R. Proksa, presented at the 2nd Workshop on Medical Applications of Spectroscopic X-ray Detectors, Europe/Zurich, (2013, unpublished); and W. Peppler, B. Kudva, J. Dobbins, C. Lee, C. Mistretta, "A Digitally Controlled Beam Attenuator," American Journal of Roentgenology 139, 426-426 (1982).

Embodiments of the subject invention provide simple, general, and easy-to-implement systems and methods for 3D bowtie attenuation. In an embodiment, a bowtie can include an HB filter filled with a liquid (e.g., a heavy liquid) and a WB filter immersed in the liquid of the HB. The combination of the HB and WB filters overcomes the drawbacks of related art devices, such as the degradation of the X-ray signal. The filters can be personalized to each object to be imaged (e.g., each individual patient, such as a human patient). This can be done using, e.g., rapid prototyping to generate the WB filter that best fits the contour of the object to be imaged. The bowtie results in a balanced flux distribution on a detector (e.g., a detector array).

When an X-ray beam irradiates an object in cone-beam geometry, the length of each X-ray path varies significantly as a function of the angular position of the ray within a tilted fan-beam, the tilting angle, and the object. If these variations are not effectively compensated, a large dynamic range will be required, or a data overflow problem will be generated in detectors. This is especially problematic for spectral detectors whose counting rates are much slower than the current integrating counterparts. To meet such a challenge, a smart bowtie, such as a bowtie of the subject invention, can be used to optimally shape the X-ray beam so that the expected numbers of photons are equalized across detector channels. A major task of the dynamic bowtie design is to determine the bowtie shape and its dynamics to undo the path length changes during a CT scan. First, a bowtie filter profile for the central beam plane in fan-beam geometry will be discussed, and then the same for cone-beam geometry will be discussed.

Figure 1B:
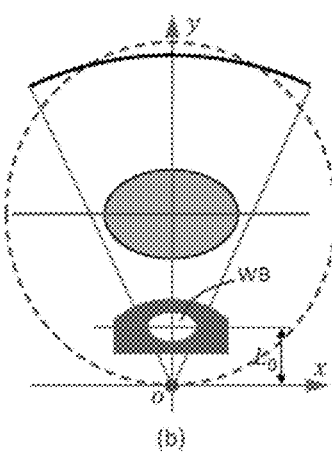
FIG. 1B shows a dynamic bowtie in fan-beam geometry.
Figure 1C:
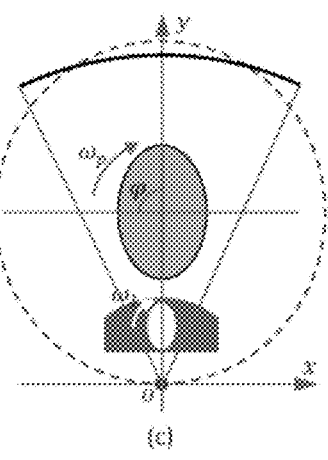
FIG. 1C shows a dynamic bowtie in fan-beam geometry.

FIGS. 1A-1C show dynamic bowties according to embodiments of the subject invention, in fan-beam geometry for a balanced flux distribution upon an equiangular detector array. FIG. 1A depicts a case where no object is in the FOV and a liquid HB is present. FIG. 1B depicts a case where an elliptical phantom is in the FOV and corresponds to the HB having a WB within it to compensate for the attenuation due to the phantom. FIG. 1C depicts a case where the WB is synchronously rotated with the gantry for dynamic compensation (e.g., $\varphi=\pi/2$).

On the central imaging plane, a multi-slice/cone-beam becomes a fan-beam. For ease of calculation, it can be assumed that the fan-beam geometry has detector cells equi-angularly distributed. An X-ray source can be rotated along a circular trajectory of radius $R_0$. Let $L(\gamma)$ denote a ray in the fan-beam, where the angle $\gamma$ specifies the ray in the fan-beam. The coordinate systems are shown established in FIGS. 1A, 1B, and 1C, where $\sigma:=\{o; x, y, z=0\}$ is fixed with the source. When no object is in the FOV, data detected can be uniform with a bowtie. Then, if an HB as shown in FIG. 1A is placed for uniform detector readings, the profile $B_h(\gamma)$ of the bowtie can be expressed in $\sigma$ as $$B_h(\gamma) = \begin{bmatrix} x_h \\ y_h \end{bmatrix} = \begin{bmatrix} S_0 \tan\gamma + B_0 \sin\gamma + x(\gamma) \\ S_0 + B_0 \cos\gamma + y(\gamma) \end{bmatrix}, \quad (1)$$

where $S_0$ is the distance from the source to the HB, $B_0$ is the attenuation length of the HB, and $x(\gamma)$ and $y(\gamma)$ define a bowtie layer to compensate for the inhomogeneous intensity distribution of x-rays from an x-ray source.

Because a cross-section of the human head, chest, and abdomen can be approximated to be elliptical, the bowtie filter can be analytically designed for such objects. Referring to FIG. 1B, when an elliptical water phantom with a semi-major axis A and a semi-minor axis B is placed within the fan-beam, the acquired data can vary according to different path lengths. Then, the fan-beam projection $P_w(\varphi, \gamma)$ through the homogenous elliptical object with an attenuation coefficient $\mu_w$ can be derived as $$P_w(\varphi, \gamma) = \quad (2)$$
$$\begin{cases} \frac{2\mu_w AB}{S^2(\varphi+\lambda)} \sqrt{S^2(\varphi+\gamma) - (R_0 \sin(\gamma))^2}, & \text{for } |R_0 \sin(\gamma)| \le S(\varphi+\gamma) \\ 0, & \text{for } |R_0 \sin(\gamma)| > S(\varphi+\gamma) \end{cases},$$

where $$S^2(\varphi+\gamma) = A^2 \cos^2(\varphi+\gamma) + B^2 \sin^2(\varphi+\gamma).$$

To make the acquired data uniform, an elliptical low attenuation chamber (the WB) with a semi-major axis a and a semi-minor axis b can be inserted into the HB. When the WB is rotated synchronously with the source, the variation of projection $P_w(\varphi,\gamma)$ can be compensated (e.g., perfectly compensated) for. For that purpose, the net projection can be expressed as $$P(\varphi,\gamma) = P_h - P_l(\varphi,\gamma) + P_w(\varphi,\gamma) \quad (3)$$

where $P_h$ is the full projection only with the HB (without a WB), which yields uniform projection data by design, and $P_l(\varphi,\gamma)$ is the differential projection of the high density liquid replaced by the WB. Let $L_0 = S_0 + B_0/2$, $\mu_h$ and $\mu_l$ be the attenuation coefficient of the HB and WB, respectively. If $$\frac{R_0}{L_0} = \frac{\mu_h - \mu_l}{\mu_w} = \frac{A}{a} = \frac{B}{b}, \quad (4)$$

which is the scaling factor from the phantom to the WB, equals the ratio between the differential value of HB with WB and the phantom in terms of the linear attenuation coefficient, then $$P_l(\varphi,\gamma) = P_w(\varphi,\gamma), \quad (5)$$

and $$P(\varphi,\gamma) = P_h = \text{const.} \quad (6)$$

That is, a constant projection profile can be present during a full scan.

Embodiments of the subject invention for fan-beam CT can include a rotating solid WB in a stationary liquid HB. A related art beam shaper by Roessl et al. (E. Roessl, R. Proksa, presented at the 2nd Workshop on Medical Applications of Spectroscopic X-ray Detectors, Europe/Zurich, (2013, unpublished)) used a circular metal piece with a reduced elliptical patient inside, which is rotated in synchrony with the source to compensate for heterogeneous x-ray path lengths through the patient and a "pre-shaper" to equalize the x-ray flux.[17] A reduced version of the object to be imaged (e.g., a patient such as a human patient) can be used for the purpose of compensation, and flux normalization can be performed. The subject invention is different from related art methods, including that of Roessl et al. (E. Roessl, R. Proksa, presented at the 2nd Workshop on Medical Applications of Spectroscopic X-ray Detectors, Europe/Zurich, (2013, unpublished)), due at least to the use of a liquid (e.g., a highly-attenuating liquid) in the HB and the fact that the bowtie can be configured for and can be used for circular and/or spiral multi-slice/cone-beam scanning.

Figure 2:
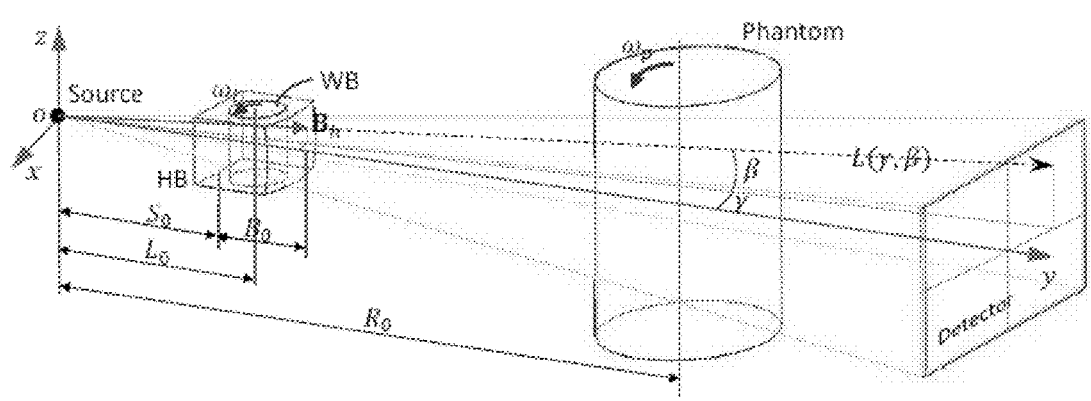
FIG. 2 shows a dynamic bowtie in cone-beam geometry with a flat panel detector plate.

The dynamic bowtie design can be extended from fan-beam geometry to multi-slice/cone-beam geometry. FIG. 2 shows a schematic of a dynamic bowtie according to an embodiment of the subject invention, in cone-beam geometry. A flat panel detector plate (labeled "Detector") is shown, though embodiments are not limited thereto. Referring to FIG. 2, the coordinate system for cone-beam CT is shown, where $\sigma:=\{o; x, y, z\}$ is fixed with the source. Let $L(\gamma,\beta)$ denote a ray within the cone-beam, where $\gamma$ and $\beta$ specifies the angle in reference to the two orthogonal central planes respectively. Similar to the fan-beam case, a surface for the HB to produce uniform detector data can be defined, and the surface $B_h(\gamma,\beta)$ of the HB can be expressed in $\sigma$ as follows:

$$B_h(\gamma,\beta) = \begin{bmatrix} x_h \\ y_h \\ z_h \end{bmatrix} = \begin{bmatrix} S_0 \tan\gamma + B_0 \cos\beta \sin\gamma + x(\gamma,\beta) \\ S_0 + B_0 \cos\beta \cos\gamma + y(\gamma,\beta) \\ \left(B_0 + \dfrac{S_0}{\cos\beta \cos\gamma}\right)\sin\beta + z(\gamma,\beta) \end{bmatrix}, \quad (7)$$

where $x(\gamma,\beta)$, $y(\gamma,\beta)$, $z(\gamma,\beta)$ define a bowtie layer for X-ray flux normalization, similar to the fan-beam case.

A cylindrical water phantom can be used, with an elliptical cross-section with a semi-major axis A and a semi-minor axis B, in the cone-beam case, because a patient is quite similar to a cylinder in terms of approximation. Then, the acquired multi-slice/cone-beam data can have more variations than in the fan-beam case. Mathematically, the multi-slice/cone-beam projection $P_w(\varphi,\gamma,\beta)$ through the homogenous cylindrical phantom with an attenuation coefficient $\mu_w$ can be obtained as $$P_w(\varphi, \gamma, \beta) = \begin{cases} \dfrac{\left(\dfrac{2u_w AB}{S^2(\varphi + \lambda)}\sqrt{S^2(\varphi + \gamma) - (R_0 \sin(\gamma))^2}\right)}{\cos \beta}, & \text{for } |R_0 \sin(\gamma)| \leq S(\varphi + \gamma), \\ 0, & \text{for } |R_0 \sin(\gamma)| > s(\varphi + \gamma) \end{cases} \quad (8)$$

where $$S^2(\varphi + \gamma) = A^2 \cos^2(\varphi + \gamma) + B^2 \sin^2(\varphi + \gamma).$$

Similar to the fan-beam case, in order to make the acquired data have identical expected values, a cylindrical WB, with a semi-major axis a and a semi-minor axis b, can be inserted into the HB. When the WB and the source are rotated in synchrony, the variation in $P_w(\varphi,\beta,\beta)$ can be appropriately canceled out. Specifically, the whole projection can be expressed as $$P(\varphi,\gamma,\beta) = P_h - P_l(\varphi,\gamma,\beta) + P_w(\varphi,\gamma,\beta). \quad (9)$$

If the parameters are set according to Equation (4), then $$P_l(\varphi,\beta,\beta) = P_w(\varphi,\gamma,\beta), \quad (10)$$

and $$P(\varphi,\gamma,\beta) = P_h = \text{const}. \quad (11)$$

Figure 3:
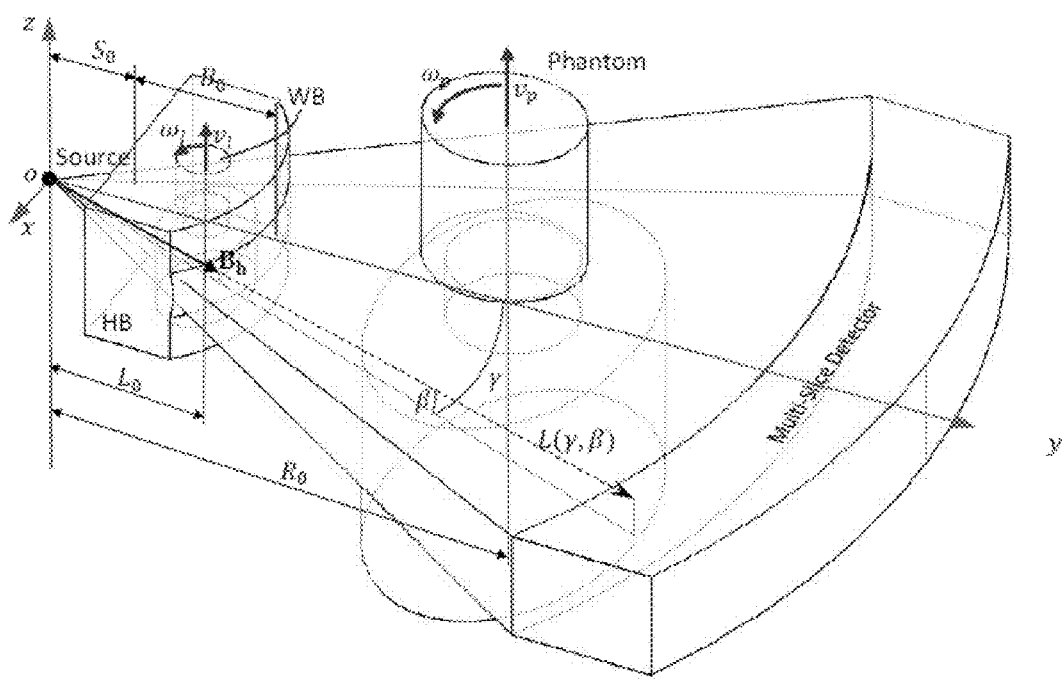
FIG. 3 shows a dynamic bowtie in a spiral multi-slice geometry with a multi-slice detector array.

FIG. 3 shows a schematic view of a dynamic bowtie according to an embodiment of the subject invention, in a spiral multi-slice geometry. A multi-slice detector array is shown, though embodiments are not limited thereto. Referring to FIG. 3, a helical multi-slice/cone-beam scan can be used with a bowtie of the subject invention. The difference between such circular and helical scans may be significant only if a longitudinally non-uniform object is imaged, such as a human patient. In this case, the WB can be a miniature of the object to be scanned, and the WB motion can be different from that for circular multi-slice/cone-beam scanning. In addition to the synchronized rotation of the WB and the source, the WB should be translated as well in synchrony with the object translation but at a slower speed. Let $p = L_0/R_0$, then $$v_l = v_p \times p, \quad (12)$$

where $v_l$ and $v_p$ are the translation speeds of the WB and the object respectively.

In many embodiments, a dynamic bowtie can be a purposely-shaped highly attenuating liquid container with a customized low attenuation bowtie inside that is configured to be, and can be, moved under precise control in synchrony with source rotation, patient translation, or both. Two major factors can be taken into account when designing a bowtie. The first factor is the selection of the highly-attenuating liquid and weakly-attenuating material, and the second is the material or materials for the container of the HB and/or the WB. For medical CT applications, the attenuation coefficients for HB and WB can be, for example, $\mu_h - \mu_l = (3\sim5)\mu_w$, which means the size of the WB is ($\frac{1}{3}$-$\frac{1}{5}$) the size of the object to be scanned. The casing material of the HB should have the same or similar attenuation characteristics as the liquid, while the attenuation coefficient of the WB should be low (e.g., as low as possible).

In many embodiments, air can be used as an ideal WB material with almost zero attenuation. For example, the WB can be an air chamber within a thin-walled low attenuation container. In an embodiment, a 3D printing technique can be used to produce an inhomogeneous WB chamber, for example to mimic a human patient to be imaged more realistically. Such a 3D printing technique that can be used is pseudo halftone, though embodiments are not limited thereto. Pseudo halftone is discussed in U.S. Pat. No. 6,724,499, which is hereby incorporated by reference in its entirety.

Figure 4A:
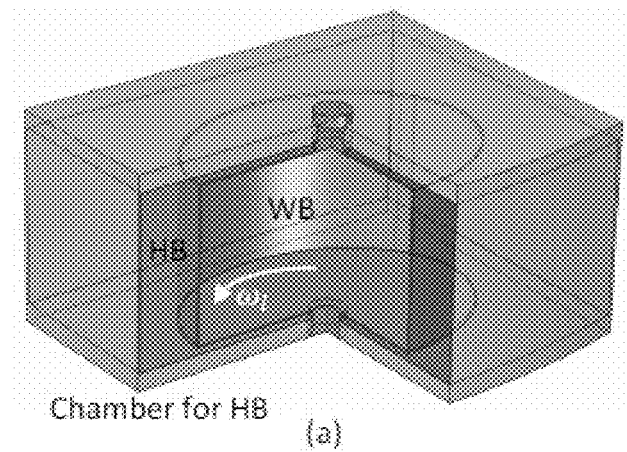
FIG. 4A shows a sectional view of a dynamic bowtie according to an embodiment of the subject invention.
Figure 4B:
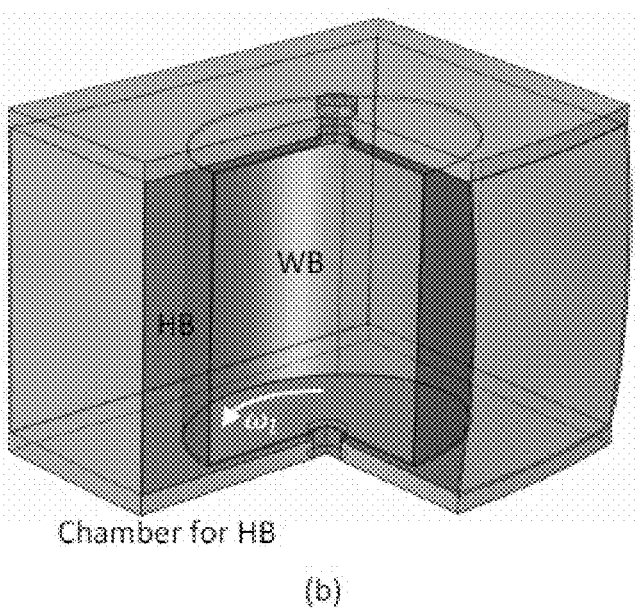
FIG. 4B shows a sectional view of a dynamic bowtie according to an embodiment of the subject invention.
Figure 4C:
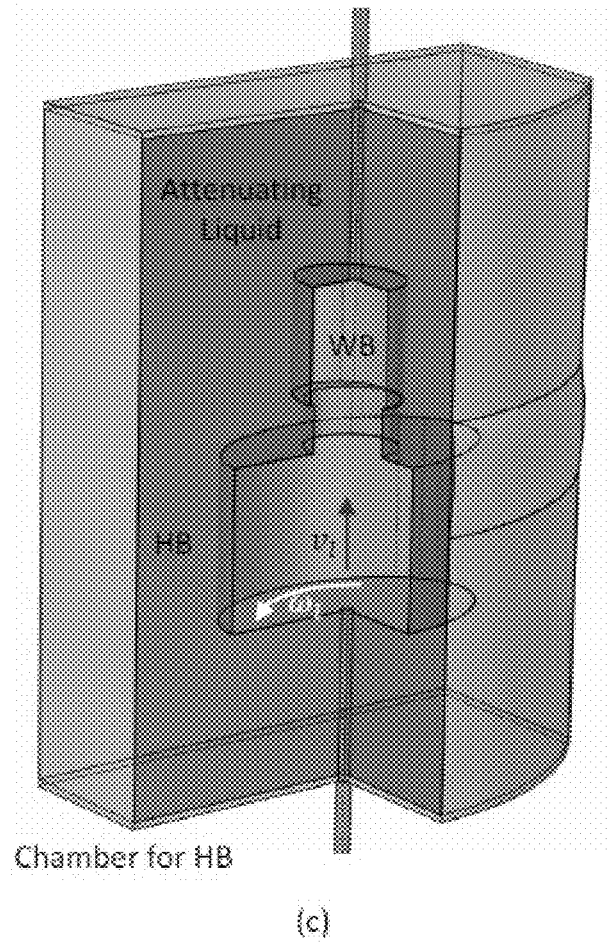
FIG. 4C shows a sectional view of a dynamic bowtie according to an embodiment of the subject invention.

FIGS. 4A-4C show schematic view of dynamic bowties according to embodiments of the subject invention; no driving components are shown. FIG. 4A shows a dynamic bowtie that can be used for fan-beam CT, FIG. 4B shows a dynamic bowtie that can be used for cone-beam CT, and FIG. 4C shows a dynamic bowtie that can be used for spiral, multi-slice CT. These bowties are shown as examples only and should not be construed as limiting. That is, other shapes and configurations of a bowtie can be used for each type of CT. Referring to FIGS. 4A-4C, the HB can be a container with liquid provided therein. The WB can be disposed within the liquid of the HB and can be a container as well. The WB can contain liquid, solid, or, preferably, air. The container of the HB can be made of a suitable material, such as aluminum (e.g., having a thickness of 0.5 mm or less), though embodiments are not limited thereto. The container of the WB can be made of a suitable material, such as plastic (e.g., having a thickness of 0.2 mm or less), though embodiments are not limited thereto. The plastic of the WB can be, for example, C-552 air-equivalent plastic, though embodiments are not limited thereto. The liquid of the HB can be, for example a heavy liquid, such as a cerous chloride ($CeCl_3$) solution, which is quite soluble, though embodiments are not limited thereto. CeCl3 can be used because it is quite soluble. The attenuation coefficient can be obtained by adjusting the concentration of the liquid of the HB (e.g., by adjusting the concentration of a $CeCl_3$ solution), and the attenuation coefficient can be obtained such that, for example, $\mu_h - \mu_l = (3\sim5)\mu_w$.

Embodiments of the subject invention provide systems and methods of imaging including a dynamic bowtie that has an HB and a WB. The HB can be liquid (e.g., liquid contained within a container), and the WB can be a rotating or spiraling WB disposed in the liquid of the HB. For a clinical CT scan, the WB can be individualized before imaging. With the progress of 3D surface scanning of a human body, and the popularization of 3D printing technology, a WB can be customized to the object to be scanned (e.g., a human patient) and then 3D printed to provide for the best possible bowtie. That is, dynamic bowties can be individualized via rapid prototyping based on an individualized optical surface model. In an embodiment, this process can be completely automatic and completed quickly (e.g., possibly in a matter of minutes, such as a few minutes). That is, the body surface of a patient can be captured, a digital atlas (such as the visible human dataset) can be deformed into the surface model, and the rotating patient-specific WB can be produced (e.g., 3D printed).

Figure 10:
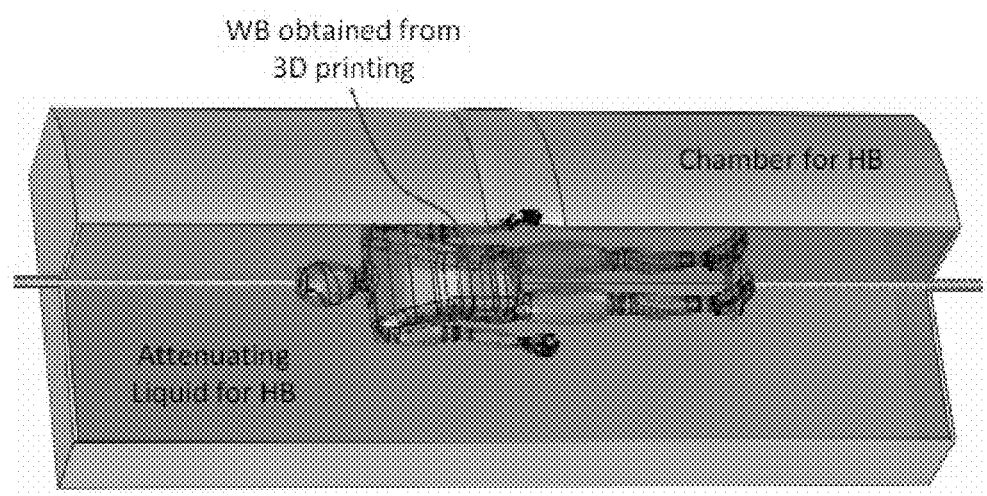
FIG. 10 shows a schematic view of a dynamic bowtie according to an embodiment of the subject invention.

FIG. 10 shows a dynamic bowtie according to an embodiment of the subject invention. Referring to FIG. 10, the bowtie can be used for full body helical CT, in which the WB is rapidly prototyped according to an individualized patient contour obtained from surface scanning. As discussed, the WB can be a reduced copy of the object to be scanned (e.g., a patient, such as a human patient). During helical cone-beam scanning, the WB movement can be fully synchronized with the helical scanning trajectory from the beginning to the end. The geometrical adaptability and technical feasibility of the 3D dynamic bowties of the subject invention provides significant performance improvement and dose saving.

Embodiments of the subject invention provide methods and systems using dynamic bowties for multi-slice/cone-beam CT (e.g., in circular or helical scanning mode). A 3D WB that is a miniature of an object being scanned (e.g., a patient, such as a human patient) can be disposed in a liquid HB, and the motions of the WB and the object being scanned can be coordinated to compensate for any attenuation path differences.

Systems and methods of the subject invention increase safety by reducing the amount of radiation dose to which the object (e.g., a human patient) is exposed, thereby decreasing the risk of developing cancer due to radiation exposure. Images produced have higher quality as the readings in the detectors are equalized, and beam hardening is reduced, addressing one of the most commonly-encountered artifacts in CT scanning.

Systems and methods of the subject invention can be used in many applications, including but not necessarily limited to: CT scanning (e.g., CT diagnostic applications); gamma knife treatment in oncology, with the goal of minimizing radiation reaching healthy tissue; high-intensity, focused ultrasound applications for therapeutic purposes (e.g., to minimize the high-intensity ultrasound reaching tissue that should not be treated); and other industrial applications for which CT is commonly used (e.g., geological investigation).

The subject invention includes, but is not limited to, the following exemplified embodiments.

Embodiment 1

A dynamic bowtie filter for computed tomography (CT), comprising:
a highly-attenuating bowtie (HB) comprising a liquid contained within a first container; and
a weakly-attenuating bowtie (WB) immersed within the liquid of the HB and comprising a second container.

Embodiment 2

The dynamic bowtie filter according to embodiment 1, wherein the WB comprises air within the second container, such that the WB is an air chamber.

Embodiment 3

The dynamic bowtie filter according to any of embodiments 1-2, wherein the WB is configured to rotate in synchrony with a radiation source during CT scanning.

Embodiment 4

The dynamic bowtie filter according to any of embodiments 1-3, wherein the WB is configured to translate in synchrony with an object to be imaged during CT scanning.

Embodiment 5

The dynamic bowtie filter according to any of embodiments 1-4, wherein the WB is a scaled-down version of an object to be imaged during CT scanning.

Embodiment 6

The dynamic bowtie filter according to any of embodiments 1-5, wherein the WB is a ⅓ to ⅕ scale version of an object to be imaged during CT scanning.

Embodiment 7

The dynamic bowtie filter according to any of embodiments 1-6, wherein the first container is an aluminum container.

Embodiment 8

The dynamic bowtie filter according to any of embodiments 1-7, wherein each wall of the first container has a thickness of 0.5 millimeters (mm) or less.

Embodiment 9

The dynamic bowtie filter according to any of embodiments 1-8, wherein the second container is a plastic container.

Embodiment 10

The dynamic bowtie filter according to any of embodiments 1-9, wherein each wall of the second container has a thickness of 0.2 millimeters (mm) or less.

Embodiment 11

The dynamic bowtie filter according to any of embodiments 1-10, wherein the liquid of the HB has a density that is greater than that of water.

Embodiment 12

The dynamic bowtie filter according to any of embodiments 1-11, wherein the liquid of the HB is $CeCl_3$.

Embodiment 13

The dynamic bowtie filter according to any of embodiments 1-12, wherein the second container is a C-552 air-equivalent plastic container.

Embodiment 14

The dynamic bowtie filter according to any of embodiments 1-13, wherein at least one of the HB and the WB is fabricated by 3D printing based on a 3D surface scan of an object to be imaged.

Embodiment 15

A computed tomography (CT) imaging device, comprising:
a radiation source;
a detector to receive radiation after it passes through an object to be imaged; and the dynamic bowtie filter according to any of embodiments 1-14

Embodiment 16

The CT imaging device according to embodiment 15, wherein the radiation source is an X-ray source.

Embodiment 17

A method of imaging an object using CT, the method comprising:
positioning the object within the field of view (FOV) of the CT imaging device according to embodiment 15; and
providing radiation from the radiation source such that the detector receives at least a portion of the radiation after it passes through the object.

Embodiment 18

The method according to embodiment 17, wherein the WB rotates in synchrony with the radiation source while the radiation source provides radiation, and
wherein the WB translates in synchrony with the object while the radiation source provides radiation.

Embodiment 19

The method according to any of embodiments 17-18, wherein the object is a human patient.

Embodiment 20

The method according to any of embodiments 17-19, further comprising:
performing three-dimensional (3D) surface scanning on the object to obtain a 3D surface scan of the object; and
fabricating the WB of the dynamic bowtie filter of the CT imaging device by 3D printing a scaled-down version of the object based on the 3D surface scan of the object Embodiment 21

The method according to embodiment 20, wherein 3D surface scanning is performed on the object before providing radiation from the radiation source.

Embodiment 22

The method according to any of embodiments 20-21, wherein the WB is fabricated before (and optionally during and/or after) providing radiation from the radiation source.

Embodiment 23

The method according to any of embodiments 20-22, wherein 3D surface scanning is performed on the object before (and optionally during and/or after) positioning the object within the FOV of the CT imaging device.

Embodiment 24

The method according to any of embodiments 20-23, wherein the WB is fabricated before (and optionally during and/or after) positioning the object within the FOV of the CT imaging device.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

A dynamic bowtie was designed and tested using simulation software. The dynamic bowtie was designed similar to that shown in FIG. 2, using the parameters listed in Table 1. To simulate the dynamic range of detector readings, a mono-energetic X-ray tube was assumed to work at 100 keV, and the numbers of detected photon were the same $I_0$ without a bowtie for a blank scan. The WB was an air chamber with attenuation coefficient $\mu_l=0$, and the bowtie was designed with the liquid (of the HB) of attenuation coefficient $\mu_h=3\mu_w$, for a water cylinder (object to be imaged) of an elliptical cross-section of a semi-major axis A=200 mm and a semi-minor axis B=160 mm.

TABLE 1

Parameters used for the design of a dynamic bowtie.

| Parameter | Value |
| --- | --- |
| Source trajectory | Full circle |
| Scan radius ($R_0$) | 57 cm |
| Source to detector distance (SDD) | 114 cm |
| X-ray energy (keV) | 100 |
| Number of projections | 1160 |
| Number of detector pixels | 672*100 |
| Detector slice thickness (Δh) | 2 mm |
| Detector angular aperture (Δγ) | 1.354 × 10⁻³ radian |
| HB container material | Aluminum |
| HB container thickness ($t_{hb}$) | 0.05 cm |
| HB container attenuation ($\mu_{hb}$) [21] | 0.460 cm⁻¹ |
| HB liquid attenuator | CeCl₃ solution |
| HB liquid attenuation ($\mu_h$) | $3\mu_w$ |
| HB attenuation length ($B_0$) | 14 cm |
| WB attenuator | Air |
| WB container material | C-552 air-equivalent plastic |
| WB container thickness ($t_{lb}$) | 0.02 cm |
| WB container attenuation ($\mu_{lb}$) [20] | 0.112 cm⁻¹ |
| Water attenuation coefficient ($\mu_w$) [22] | 0.171 cm⁻¹ |
| Source to bowtie distance ($S_0$) | 12 cm |

Figure 5A:
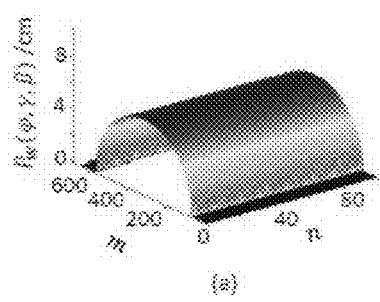
FIG. 5A shows a surface display projection of the sinogram of an elliptical water phantom for $\varphi=0$.
Figure 5B:
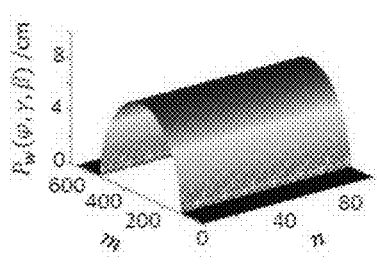
FIG. 5B shows a surface display projection of the sinogram of an elliptical water phantom for $\varphi=\pi/2$.
Figure 5C:
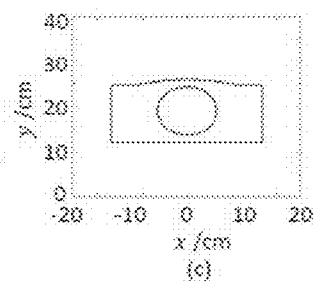
FIG. 5C shows a bowtie profile for $\varphi=0$ and $\beta=0$.

FIGS. 5A and 5B show projections of the elliptical water phantom for φ=0 and φ=π/2, respectively, and FIG. 5C shows the bowtie profile for φ=0 and β=0. The projection angle φ can be indexed by the projection number, i (0≤i<1160), φ=i×Δφ, Δφ=2π/1160). The ray angle γ can be indexed by the horizontal detector number, γ=(335−m)×Δγ, (0≤m<672). The ray angle β can be indexed by the vertical detector number, $$\beta = (n-49) \times \mathrm{atan}\left(\frac{\Delta h}{SDD}\right), (0 \le n < 100).$$

FIGS. 5A and 5B show the projection profiles $P_w(\varphi,\gamma,\beta)$ of the water phantom without any bowtie. Setting the projection angle φ=0 and the fan angle γ=0, the minimum projection value along the central ray $P_w(0,0,0)$ was obtained. Setting φ=π/2 and γ=0, the maximum value along the central ray $P_w(\pi/2,0,0)$ was obtained.

The side of the HB facing the source was assumed flat for convenience. Then, the surface of HB $B_h(\gamma,\beta)$ was computed using Equation (7). The WB was rotated angularly around the axis perpendicularly through the bowtie center. Using Equation (4), the WB was considered an elliptical chamber scaled down from an object by a factor of ⅓ of the object, which means an elliptical cylinder chamber with a semi-major axis a=66.667 mm and a semi-minor axis b=53.333 mm. FIG. 5C shows a visualization of the bowtie for $\varphi=0$ and $\beta=0$.

Figure 6A:
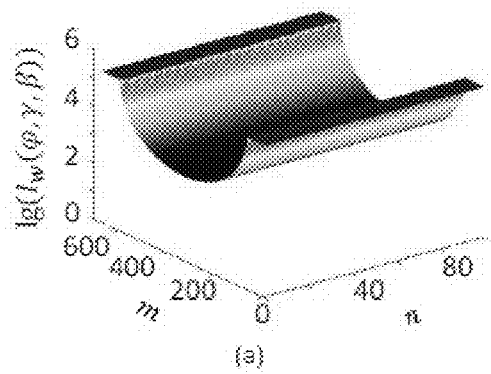
FIG. 6A shows a surface display for detected photons, without any bowtie, for $\varphi=0$.
Figure 6B:
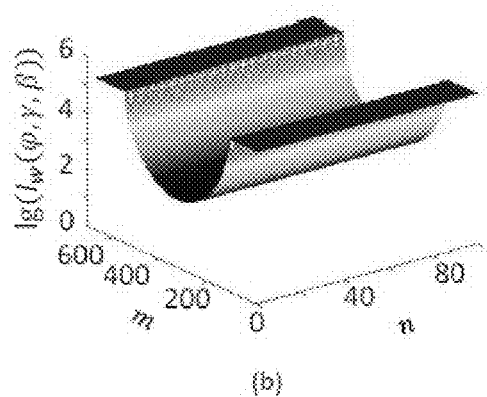
FIG. 6B shows a surface display for detected photons, without any bowtie, for $\varphi=\pi/2$.

First, the numbers of detected photons without the dynamic bowtie were calculated for the water phantom of A=200 mm and B=160 mm over a full scan. By Beer's law, $$I_w(\varphi,\gamma,\beta)=I_0 e^{-P_w(\varphi,\gamma,\beta)}, \quad (13)$$

the numbers of projection data were synthesized, as plotted in FIGS. 6A and 6B for $\varphi=0$ and $\varphi=\pi/2$, respectively, assuming the number of emitted photons per second $I_0=2\times 10^5$ along each ray path. That is, FIGS. 6A and 6B show the numbers of detected photons along X-rays through the water phantom without any bowtie (on a log scale) for $\varphi=0$ and $\varphi=\pi/2$, respectively.

Second, with the dynamic bowtie for the aforementioned phantom and $I_0=2\times 10^7$ (the increment in the flux is to overcome the attenuation of the bowtie), the numbers of photons were simulated again for each ray path. The container materials of the HB and WB do have some effect. By Equation (11), $$I(\varphi,\gamma,\beta)=I_0 e^{-(P_h(\gamma,\beta)+P_{lt}(\varphi,\gamma,\beta))}, \quad (14)$$

where $P_h(\gamma,\beta)$ is the projection of the HB, $P_{lt}(\varphi,\gamma,\beta)$ is the projection of the WB container, and $$P_h(\gamma,\beta) = B_0 \times \mu_h + \left(1+\frac{1}{\cos\gamma\times\cos\beta}\right)\times t_{hb}\times(\mu_{hb}-\mu_h), \quad (15)$$

$$P_{lt}(\varphi,\gamma,\beta) = \begin{cases} 0, & \text{for } |L_0\sin(\gamma)| > s(\varphi+\gamma) \\ \dfrac{\left(\dfrac{2ab}{s^2(\varphi+\lambda)}\sqrt{s^2(\varphi+\gamma)-(L_0\sin(\gamma))^2}\right)}{\cos\beta}\mu_{lb} & \text{for } |L_0\sin(\gamma)| \le s(\varphi+\gamma) \text{ and } |L_0\sin(\gamma)| > s_l(\varphi+\gamma) \\ \dfrac{\left(\left(\dfrac{2ab}{s^2(\varphi+\lambda)}\sqrt{s^2(\varphi+\gamma)-(L_0\sin(\gamma))^2}\right)-\left(\dfrac{2a_l b_l}{s_l^2(\varphi+\lambda)}\sqrt{s^2(\varphi+\gamma)-(L_0\sin(\gamma))^2}\right)\right)}{\cos\beta}\mu_{lb} & \text{otherwise} \end{cases},$$

where $$s^2(\varphi+\gamma)=a^2\cos^2(\varphi+\gamma)+b^2\sin^2(\varphi+\gamma),\ s_l^2(\varphi+\gamma)=a_l^2\cos^2(\varphi+\gamma)+b_l^2\sin^2(\varphi+\gamma),$$

$$a_l = a - t_{lb},\ b_l = b - t_{lb}.$$

From Equations (14)-(16), when $\mu_{hb}\to\mu_{lb}$ and $t_{lb}$ are small enough, $I(\varphi,\gamma,\beta)\approx \text{const}$, which means that the numbers of detected photons can be effectively regulated along each ray path through the water phantom.

Figure 7A:
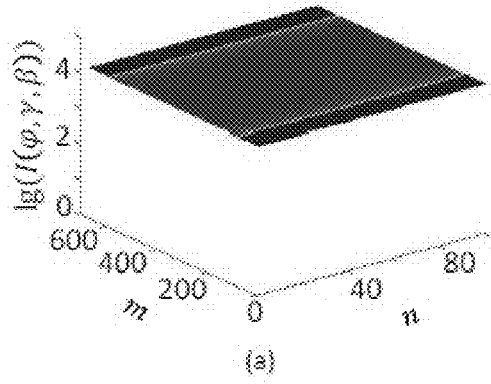
FIG. 7A shows a surface display for detected photons, with a bowtie according to an embodiment of the subject invention, for $\varphi=0$.
Figure 7B:
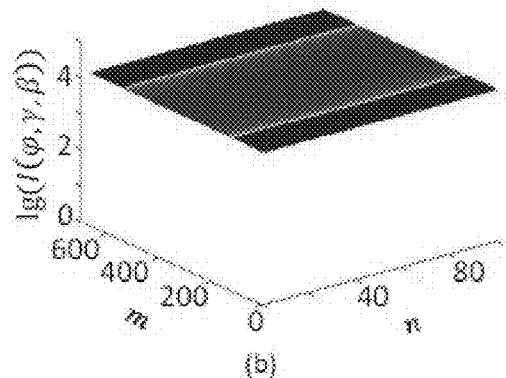
FIG. 7B shows a surface display for detected photons, with a bowtie according to an embodiment of the subject invention, for $\varphi=\pi/2$.

FIGS. 7A and 7B show numbers of detected photons $I(\varphi,\gamma,\beta)$ along X-rays through the water phantom with the dynamic bowtie (on a log scale) for $\varphi=0$ and $\varphi=\pi/2$, respectively. Referring to FIGS. 7A and 7B, the numbers of detected photons were made quite uniform with only slight variations mainly due to the container material for WB. It is plainly feasible to make the expected numbers of detected photons almost the same across all the detector elements with a dynamic bowtie according to an embodiment of the subject invention. If a cross section of a patient can be well-approximated in this way, the dynamic range of detectors can be optimally matched to that of projection data.

Example 2

Figure 8:
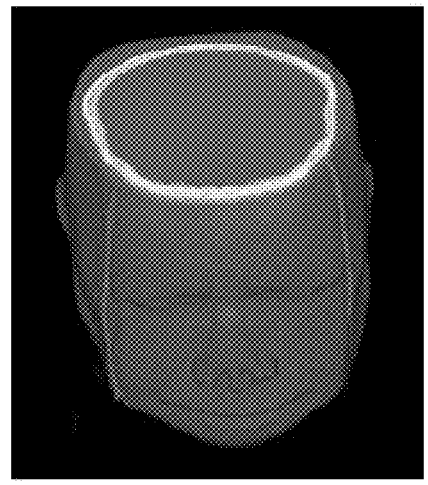
FIG. 8 shows a head CT model.

To show the practical value of the 3D dynamic bowtie, the bowtie of Example 1 was used for a 3D CT imaging volume. The detected photons were simulated, and the dynamic ranges of the signals with and without the dynamic bowtie were compared. FIG. 8 is a 3D head CT volume from the Visible Human project (www.ntis.gov/products/vishuman.aspx). After scaling, the head was approximated as a cylinder with an elliptical cross-section of a semi-major axis A=102 mm and a semi-minor axis B=81 mm. The dynamic bowtie in Example 1 was designed for the cylindrical water phantom of A=102 mm and B=81 mm.

Figure 9A:
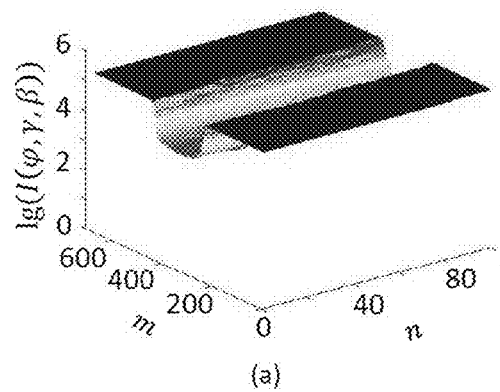
FIG. 9A shows a surface display for detected photons along X-rays through a water phantom, without any bowtie, for φ=0.
Figure 9B:
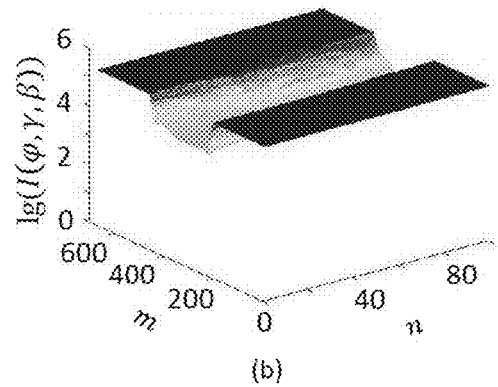
FIG. 9B shows a surface display for detected photons along X-rays through a water phantom, without any bowtie, for φ=π/2.
Figure 9C:
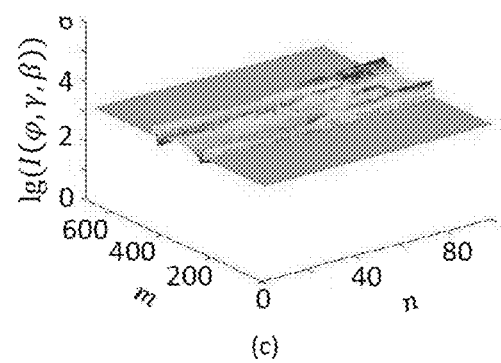
FIG. 9C shows a surface display for detected photons along X-rays through a water phantom, with a bowtie according to an embodiment of the subject invention, for φ=0.
Figure 9D:
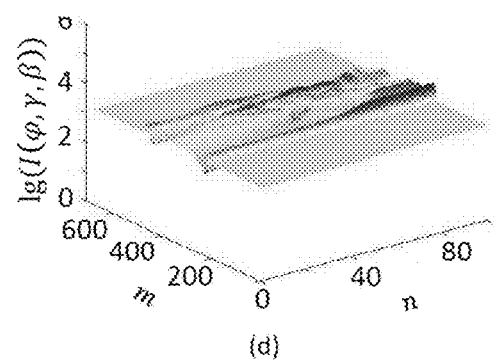
FIG. 9D shows a surface display for detected photons along X-rays through a water phantom, with a bowtie according to an embodiment of the subject invention, for φ=π/2.

FIGS. 9A and 9B show numbers of detected photons along X-rays through the water phantom without a bowtie (on a log scale), assuming $I_0=2\times 10^5$, for $\varphi=0$ and $\varphi=\pi/2$, respectively. FIGS. 9C and 9D show numbers of detected photons with a bowtie according to an embodiment of the subject invention, assuming $I_0=2\times 10^6$, for $\varphi=0$ and $\varphi=\pi/2$, respectively. Referring to FIGS. 9A-9D, the dynamic ranges of the signals differ in the two cases, showing the advantage of the use of the dynamic bowtie of the subject invention when imaging a human patient (see, e.g., FIGS. 9C and 9D). Without a bowtie, only a small portion of the detector dynamic range was utilized to depict the signal variation. With a dynamic bowtie according to an embodiment of the subject invention, the dynamic range problem was effectively resolved, leading to a reduced radiation dose for a given image quality requirement.

Although a monochromatic X-ray source has been assumed in this example and in Example 1, the advantages of the bowties of the subject invention are applicable to a polychromatic X-ray source. In practice, the multi-energy spectrum can introduce an additional layer of complexity, and in this scenario, the HB liquid and WB content can be matched while keeping in mind the X-ray spectrum. Also, the objective function can be augmented in terms of numbers of detected photons, and the least square criterion can be utilized for an overall optimization.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1 A. Berrington de Gonzalez, S. Darby, "Risk of cancer from diagnostic X-rays: estimates for the UK and 14 other countries," Lancet 363, 345-351 (2004).
2 R. Ballabriga, M. Campbell, E. Heijne, X. Llopart, L. Tlustos, W. Wong, "Medipix3: A 64 k pixel detector readout chip working in single photon counting mode with improved spectrometric performance," Nuclear Instruments & Methods in Physics Research Section a-Accelerators Spectrometers Detectors and Associated Equipment 633, S15-S18 (2011).
3 K. Taguchi, E. C. Frey, X. L. Wang, J. S. Iwanczyk, W. C. Barber, "An analytical model of the effects of pulse pileup on the energy spectrum recorded by energy resolved photon counting x-ray detectors," Medical Physics 37, 3957-3969 (2010).
4 J. Hsieh, Computed Tomography: Principles, Design, Artifacts, and Recent Advances, 2nd Edition. (Society of Photo Optical Instrumentation Engineering, 2009).
5 S. Mutic, J. R. Palta, E. K. Butker, I. J. Das, M. S. Huq, L. N. D. Loo, B. J. Salter, C. H. McCollough, J. Van Dyk, "Quality assurance for computed-tomography simulators and the computed tomography-simulation process: Report of the AAPM radiation therapy committee task group no. 66," Medical Physics 30, 2762-2792 (2003).
6 M. Blessing, M. S. Bhagwat, Y. Lyatskaya, J. R. Bellon, J. Hesser, P. Zygmanski, "Kilovoltage beam model for flat panel imaging system with bow-tie filter for scatter prediction and correction," Physica Medica-European Journal of Medical Physics 28, 134-143 (2012).
7 J. M. Boone, "Method for evaluating bow tie filter angle-dependent attenuation in CT: Theory and simulation results," Medical Physics 37, 40-48 (2010).
8 S. Bartolac, S. Graham, J. Siewerdsen, D. Jaffray, "Fluence field optimization for noise and dose objectives in CT," Medical Physics 38, S2-S17 (2011).
9 S. E. McKenney, A. Nosratieh, D. Gelskey, K. Yang, S.-y. Huang, L. Chen, J. M. Boone, "Experimental validation of a method characterizing bow tie filters in CT scanners using a real-time dose probe," Medical Physics 38, 1406-1415 (2011).
10 M. Gies, W. A. Kalender, H. Wolf, C. Suess, M. T. Madsen, "Dose reduction in CT by anatomically adapted tube current modulation. I. Simulation studies," Medical physics 26, 2235 (1999).
11 W. A. Kalender, H. Wolf, C. Suess, "Dose reduction in CT by anatomically adapted tube current modulation. II. Phantom measurements," Medical physics 26, 2248 (1999).
12 G. S. L. Zeng, "Nonuniform noise propagation by using the ramp filter in fan-beam computed tomography," Ieee Transactions on Medical Imaging 23, 690-695 (2004).
13 T. Toth, E. Cesmeli, A. Ikhlef, T. Horiuchi, M. Flynn, "Image quality and dose optimization using novel x-ray source filters tailored to patient size," Medical Imaging 2005: Physics of Medical Imaging, Pts 1 and 2 5745, 283-291 (2005).
14 N. Mail, D. J. Moseley, J. H. Siewerdsen, D. A. Jaffray, "The influence of bowtie filtration on cone-beam CT image quality," Medical Physics 36, 22-32 (2009).
15 S. S. Hsieh, N. J. Pelc, "The feasibility of a piecewise-linear dynamic bowtie filter," Medical Physics 402013).
16 F. Liu, G. Wang, W. Cong, S. Hsieh, N. Pelc, "Dynamic bowtie for fan-beam CT," Journal of X-Ray Science and Technology 21, 579-590 (2013).
17 E. Roessl, R. Proksa, presented at the 2nd Workshop on Medical Applications of Spectroscopic X-ray Detectors, Europe/Zurich, 2013 (unpublished).
18 W. PEPPLER, B. KUDVA, J. DOBBINS, C. LEE, C. MISTRETTA, "A DIGITALLY CONTROLLED BEAM ATTENUATOR," American Journal of Roentgenology 139, 426-426 (1982).
19 A. C. Kak, M. Slaney, Society for Industrial and Applied Mathematics., "Principles of computerized tomographic imaging," in Classics in applied mathematics 33. (Society for Industrial and Applied Mathematics (SIAM, 3600 Market Street, Floor 6, Philadelphia, Pa. 19104), Philadelphia, Pa., 2001), pp. 1 electronic text (xiv, 327 p.).
20 "http://physics.nist.gov/PhysRefData/XrayMassCoef/ComTab/c552.html."
21 "http://physics.nist.gov/PhysRefData/XrayMassCoef/ElemTab/z13."
22 "http://physics.nist.gov/PhysRefData/XrayMassCoef/ElemTab/water.html."
23 C. Mavroidis, R. Ranky, M. Sivak, B. Patritti, J. DiPisa, A. Caddle, K. Gilhooly, L. Govoni, S. Sivak, M. Lancia, R. Drillio, P. Bonato, "Patient specific ankle-foot orthoses using rapid prototyping," Journal of Neuroengineering and Rehabilitation 82011).
24 C. Gaisberger, P. Steininger, B. Mitterlechner, S. Huber, H. Weichenberger, F. Sedlmayer, H. Deutschmann, "Three-dimensional surface scanning for accurate patient positioning and monitoring during breast cancer radiotherapy," Strahlentherapie Und Onkologie 189, 887-893 (2013).
25 R. Bogue, "3D printing: the dawn of a new era in manufacturing?," Assembly Automation 33, 307-311 (2013).
26 W. Wang, T. Wang, Z. Yang, L. Liu, X. Tong, W. Tong, J. Deng, F. Chen, X. Liu, "Cost-effective Printing of 3D Objects with Skin-Frame Structures," Acm Transactions on Graphics 322013).
27 http://www.toshibamedicalsystems.com/tmd/english/products/dose/lowdose/hardware.html]
28 Dynamic Bowtie Filter for Cone-Beam/Multi-Slice CT—http://journals.plos.org/plosone/article?id=10.1371/journal.pone.0103054
29 Dynamic Bowtie for Fan-beam CT—http://arxiv.org/ftp/arxiv/papers/1304/1304.7701.pdf
30 The influence of bowtie filters on x-ray CT signals—http://www.ncbi.nlm.nih.gov/pubmed/19235370 Cone Beam Reconstruction (GE): http://www.aapm.org/meetings/05AM/pdf/18-2804-6504-616.pdf

What is claimed is:
1. A dynamic bowtie filter for computed tomography (CT), comprising:
a highly-attenuating bowtie (HB) comprising a liquid contained within a first container; and
a weakly-attenuating bowtie (WB) immersed within the liquid of the HB and comprising a second container;
wherein the WB is a ⅓ to ⅕ scale version of a 3D surface scan of an object to be imaged during CT scanning.

2. The dynamic bowtie filter according to claim 1, wherein the WB comprises air within the second container, such that the WB is an air chamber.

3. The dynamic bowtie filter according to claim 1, wherein the WB is configured to rotate in synchrony with a radiation source during CT scanning.

4. The dynamic bowtie filter according to claim 1, wherein the WB is configured to translate in synchrony with an object to be imaged during CT scanning.

5. The dynamic bowtie filter according to claim 1, wherein the first container is an aluminum container.

6. The dynamic bowtie filter according to claim 5, wherein each wall of the first container has a thickness of no more than about 0.5 millimeters (mm).

7. The dynamic bowtie filter according to claim 1, wherein the second container is a plastic container.

8. The dynamic bowtie filter according to claim 7, wherein each wall of the second container has a thickness of no more than about 0.2 millimeters (mm).

9. The dynamic bowtie filter according to claim 1, wherein the liquid of the HB has a density that is greater than that of water.

10. The dynamic bowtie filter according to claim 1, wherein the liquid of the HB is $CeCl_3$.

11. The dynamic bowtie filter according to claim 1, wherein the WB comprises air within the second container, such that the WB is an air chamber,
wherein the WB is configured to rotate in synchrony with a radiation source during CT scanning,
wherein the WB is further configured to translate in synchrony with an object to be imaged during CT scanning,
wherein the WB is a scaled-down version of an object to be imaged during CT scanning, and
wherein the liquid of the HB has a density that is greater than that of water.

12. The dynamic bowtie filter according to claim 11, wherein the first container is an aluminum container,
wherein the second container is a plastic container, and
wherein the liquid of the HB is $CeCl_3$.

13. A computed tomography (CT) imaging device, comprising:
a radiation source;
a detector to receive radiation after it passes through an object to be imaged; and a dynamic bowtie filter disposed between the radiation source and the detector such that radiation from the radiation source is attenuated by the dynamic bowtie filter,
wherein the dynamic bowtie filter comprises:
a highly-attenuating bowtie (HB) comprising a liquid contained within a first container; and
a weakly-attenuating bowtie (WB) immersed within the liquid of the HB and comprising a second container;
wherein the WB is a ⅓ to ⅕ scale version of a 3D surface scan of an object to be imaged during CT scanning.

14. The CT imaging device according to claim 13, wherein the WB comprises air within the second container, such that the WB is an air chamber,
wherein the WB is configured to rotate in synchrony with a radiation source during CT scanning,
wherein the WB is further configured to translate in synchrony with an object to be imaged during CT scanning,
and
wherein the liquid of the HB has a density that is greater than that of water.

15. The CT imaging device according to claim 14,
wherein the first container is an aluminum container,
wherein the second container is a plastic container,
wherein the liquid of the HB is $CeCl_3$, and
wherein the radiation source is an X-ray source.

16. A method of imaging an object using CT, the method comprising:
performing three-dimensional (3D) surface scanning on the object to obtain a 3D surface scan of the object;
fabricating the WB of the dynamic bowtie filter of the CT imaging device by 3D printing a ⅓ to ⅕ scale version of the object based on the 3D surface scan of the object;
positioning the object within the field of view of the CT imaging device according to claim 13; and
providing radiation from the radiation source such that the detector receives at least a portion of the radiation after it passes through the object,
wherein the WB rotates in synchrony with the radiation source while the radiation source provides radiation, and
wherein the WB translates in synchrony with the object while the radiation source provides radiation.

17. The method according to claim 16, wherein the WB comprises air within the second container, such that the WB is an air chamber,
wherein the WB is a scaled down version of the object,
wherein the liquid of the HB has a density that is greater than that of water, and wherein the object is a human patient.

* * * * *